US010583305B2

United States Patent
Liu et al.

(10) Patent No.: US 10,583,305 B2
(45) Date of Patent: Mar. 10, 2020

(54) METHOD AND APPARATUS FOR DETECTING A STATUS OF CPR CHEST COMPRESSIONS WITHOUT USING A STAND-ALONE COMPRESSION METER

(71) Applicant: KONINKLIJKE PHILIPS N.V., Eindhoven (NL)

(72) Inventors: Chenguang Liu, Bothell, WA (US); James Knox Russell, Seattle, WA (US); Dawn Blilie Jorgenson, Mercer Island, WA (US); Haris Duric, Bothell, WA (US); Stacy Earl Gehman, Seattle, WA (US); Christopher William Fleming, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 110 days.

(21) Appl. No.: 15/579,610

(22) PCT Filed: May 23, 2016

(86) PCT No.: PCT/EP2016/061604
§ 371 (c)(1),
(2) Date: Dec. 5, 2017

(87) PCT Pub. No.: WO2016/193041
PCT Pub. Date: Dec. 8, 2016

(65) Prior Publication Data
US 2018/0140857 A1 May 24, 2018

Related U.S. Application Data

(60) Provisional application No. 62/171,595, filed on Jun. 5, 2015.

(51) Int. Cl.
*A61N 1/39* (2006.01)
*A61H 31/00* (2006.01)
(Continued)

(52) U.S. Cl.
CPC ........ *A61N 1/39044* (2017.08); *A61B 5/0535* (2013.01); *A61B 5/6823* (2013.01);
(Continued)

(58) Field of Classification Search
CPC .............. A61N 1/39044; A61N 1/3925; A61B 5/0535; A61H 31/005
See application file for complete search history.

(56) References Cited

U.S. PATENT DOCUMENTS

| 2006/0025825 A1 | 2/2006 | Bowers |
| 2013/0023781 A1 | 1/2013 | Freeman et al. |
| 2014/0342330 A1 | 11/2014 | Freeman et al. |

FOREIGN PATENT DOCUMENTS

| EP | 2719326 A1 | 4/2014 |
| WO | 2012127380 A1 | 9/2012 |

OTHER PUBLICATIONS

Zhang et al: "Transthoracic Impedance for the Monitoring of Quality of Manual Chest Compression During Cardiopulmonary Resuscitation"; Resuscitation 83 (2012) pp. 1281-1286.

*Primary Examiner* — Tammie K Marlen

(57) ABSTRACT

A method and associated apparatus (12) detects the presence and quality of chest compressions during cardiopulmonary resuscitation (CPR) by analyzing existing signals in automated external defibrillator (AED) devices without using a stand-alone CPR meter. The method includes analyzing both a thoracic impedance signal and a common-mode current signal, each of which can be measured with standard AED pads (18). The method applies criteria to the measured signals, the criteria being used to select which of the measured signals to use for providing CPR chest compression detections.

10 Claims, 4 Drawing Sheets

(51) Int. Cl.
  *A61B 5/053*    (2006.01)
  *A61B 5/00*    (2006.01)
(52) U.S. Cl.
  CPC ......... *A61B 5/7257* (2013.01); *A61H 31/005*
    (2013.01); *A61N 1/3925* (2013.01); ***A61N
    1/3993*** (2013.01); *A61B 2505/01* (2013.01);
    *A61H 2201/0157* (2013.01); *A61H 2201/1207*
    (2013.01); *A61H 2201/168* (2013.01); *A61H
    2201/1619* (2013.01); *A61H 2201/5043*
    (2013.01); *A61H 2201/5048* (2013.01); *A61H
    2201/5076* (2013.01); *A61H 2201/5092*
    (2013.01); *A61H 2230/04* (2013.01)

METHOD AND APPARATUS FOR DETECTING A STATUS OF CPR CHEST COMPRESSIONS WITHOUT USING A STAND-ALONE COMPRESSION METER

CROSS-REFERENCE TO RELATED APPLICATION

This application is the U.S. National Phase application under 35 U.S.C. § 371 of International Application No. PCT/EP2016/061604, filed on May 23, 2016, which claims the priority of U.S. Provisional Application No. 62/171,595, filed Jun. 5, 2015, the entire contents of these applications are incorporated herein by reference.

The present embodiments relate generally to cardiopulmonary resuscitation (CPR) and more particularly, to a method and apparatus for detecting a status of chest compressions without using a stand-alone compression meter.

It has long been recognized that chest compressions during cardiopulmonary resuscitation must be applied at the correct time and at the correct rate to be effective. A number of devices and methods have been developed which detect and monitor chest compressions during CPR. The Q-CPR™ meter manufactured by Laerdal, Wappinger Falls, N.Y. is one such device. The Q-CPR™ meter is devised to be placed on the patient's chest and under the rescuers hands during CPR, and incorporates sensors which detect the applied force, depth, and rate of chest compressions. This information is fed back to the rescuer as guidance. Unfortunately, this device adds expense and complexity to the kit of equipment that is typically used by rescue personnel.

Other methods which use electrical signals passed between transthoracic defibrillator electrodes have also been developed for sensing CPR chest compressions. One known method is to use the transthoracic impedance (TTI) signals between the chest electrodes to detect CPR-related impedance changes. See for example "Transthoracic impedance for the monitoring of quality of manual chest compression during cardiopulmonary resuscitation" by Hehua Zhang et al., Resuscitation 83 (2012) 1281-1286. Another known method is to analyze the chest electrode signals in such a way as to separate the cardiac-related signals (e.g., electrocardiogram or ECG) and the CPR-related artifact. One such method is described by Addison in International Patent Publication WO2006085120A1 entitled "IMPROVEMENTS IN OR RELATING TO SIGNAL ANALYSIS." Unfortunately, these methods in themselves have not shown sufficient accuracy to be used on a stand-alone basis.

What is needed is a more accurate method and incorporating apparatus for detecting the presence and rate of CPR chest compressions, for the purposes of improving ongoing and future cardiac rescues. Preferably, such a method and apparatus could be integrated into existing defibrillation equipment without the need for additional stand-alone CPR compressions sensor such as the aforementioned Q-CPR™ meter.

Accordingly, an improved method and apparatus for overcoming the problems in the art is desired.

In accordance with one aspect of the present disclosure, a method and apparatus for detecting one or more of a status and/or quality of chest compressions during cardiopulmonary resuscitation comprises analyzing transthoracic impedance and common-mode current measurements in automated external defibrillator (AED) devices without using an additional, stand-alone, CPR meter, e.g., such as a CPRmeter™ device by Laerdal Medical Corporation of Wappingers Falls, N.Y. In addition, the method and apparatus can advantageously be used (i.e., when a CPR meter is unavailable) for retrospective analysis to provide a Q-CPR™ type of report in a post-rescue analysis program, such as the Event Review Pro™ software application product, by Koninklijke Philips, N.V. of Andover, Mass. The Event Review Pro™ product provides in-depth review and reporting, including a wide range of report types, both at the case and institution level to add to a patient's medical record, submit to national registries, and help refine training curriculum/improve code response.

The method and apparatus according to the embodiments of the present disclosure can also be incorporated into an AED to provide feedback about the quality of CPR chest compressions for a given resuscitation event in real-time. According to one embodiment, the method analyses a thoracic impedance signal (e.g., a first characteristic signal) and a common-mode current signal (e.g., a second characteristic signal), each of which can be measured with the use of standard AED pads or electrodes. Subsequent to analyzing the characteristic signals, the method and apparatus apply criteria to the analyzed first and second signals, wherein the criteria is used to select which of the first or second characteristic signals to use for providing CPR detections with improved accuracy for a given resuscitation procedure.

Thoracic impedance (also referred to as transthoracic impedance or TTI) can be measured by AED devices using standard AED electrode pads. In addition, it is also possible to measure a common-mode current using standard AED pads. The inventors have realized that, due to the varieties of the patients' position, size, the environment, the location of the AED shock pads, the site for performing compression, etc. for a given resuscitation event, the transthoracic impedance (TTI) can sometimes better reflect the artifacts caused by compression than does the common-mode current, and sometimes the opposite case is present. The inventors have further realized the advantage of utilizing both measurements, wherein the use of both measurements will result in an improved detection of compressions than using only one measurement alone. For example, the inventors have recognized that in approximately 10% of CPR events, the common-mode current is better than TTI at detecting the presence and rate of CPR chest compressions.

The inventors have also realized that the improved CPR chest compressions detection may be incorporated into an ECG analysis algorithm which analyzes through a CPR artifact. The Advanced Resuscitation Therapy (ART) algorithm, for example, may be susceptible to increased false positive "shock advised" indications in the presence of an artifact associated with very high rates of CPR chest compressions. The ART algorithm may be improved further by using the more accurate CPR parameter detection method according to the embodiments of the present disclosure. In particular, the ART algorithm may be improved, for example, by modifying its sensitivity and specificity limits for shockable rhythms in the presence of detected very high CPR rates. One example of an ART algorithm implementation in an AED is described in U.S. Provisional Patent Application No. 62/120,397, entitled "AUTOMATED EXTERNAL DEFIBRILLATOR (AED) WITH DUAL ECG ANALYSIS ALGORITHMS," which is incorporated herein by reference.

According to one embodiment of the present disclosure, an automated external defibrillator device is provided with a feature for detecting at least one of a status and a quality of cardiopulmonary resuscitation chest compressions. The AED device comprises a front end circuit, an analysis circuit, and an output device. The front end circuit is configured to obtain, via a pair of AED electrodes (i.e., in response to being coupled to an emergency care patient's chest), at least one of (i) a stream of raw transthoracic impedance data and (ii) a stream of common-mode current data. The analysis circuit is configured to process the at least one of (i) the stream of raw transthoracic impedance data and (ii) the stream of common-mode current data for correlated CPR chest compression artifacts through first and second processing algorithms. The first processing algorithm comprises a temporal peak detection algorithm to obtain at least one stream of detected compression event candidates. The second processing algorithm comprises a frequency analysis algorithm to identify false positive compression events within the at least one stream of detected compression event candidates. The analysis circuit is further configured to remove the identified false positive compression events from the at least one stream of detected compression event candidates. In addition, the output device is configured to output an indication of at least one of a status and a quality of CPR chest compressions determined in response to the at least one stream of detected compression event candidates, devoid of the identified false positive compression events.

In another embodiment, the front end circuit is further configured to obtain both (i) the stream of raw transthoracic impedance data and (ii) the stream of common-mode current data. In this embodiment, the analysis circuit is further configured to process both (i) the stream of raw transthoracic impedance data and (ii) the stream of common-mode current data to obtain respective first and second streams of detected compression event candidates. The analysis circuit is also configured to identify false positive compression events within the respective first and second streams of detected compression event candidates. The analysis circuit is further configured to remove the identified false positive compression events from respective first and second streams of detected compression event candidates. The analysis circuit also compares the first stream of detected compression event candidates, devoid of the respective identified false positive compression events, against the second stream of detected compression event candidates, devoid of the respective identified false positive compression events, to identify an optimized stream of detected compression event candidates between the first and second streams. In addition, the output device is configured to output the indication determined in response to the optimized stream of detected compression event candidates, devoid of false positive compression events.

According to another embodiment, the analysis circuit identifies an optimized stream of detected compression event candidates between the first and second streams by (i) applying a criterion to the first and second streams and (ii) selecting one of the first and second streams based upon the applied criterion to identify the optimized stream. For example, the criterion can comprise a determined autocorrelation strength similar to a predicted CPR rate period.

In yet another embodiment, the AED device further comprises an electrocardiogram (ECG) shock analysis circuit. The ECG shock analysis circuit is configured to determine a shockable ECG event in response to an ECG signal obtained via the pair of AED electrodes in the presence of CPR-related signal artifacts. The ECG shock analysis circuit is also configured to dynamically adjust a shock decision parameter in response to one or more of (a) the at least one stream of detected compression event candidates, devoid of the identified false positive compression events, and (b) the indication of the at least one of a status and a quality of CPR chest compressions. In one embodiment, the optimized stream of detected compression event candidates may be indicative of a CPR chest compression rate that is outside of a CPR protocol standard rate.

According to further embodiments, an indication of the status includes an indication that CPR chest compressions are being performed, and an indication of a quality of CPR chest compressions includes an indication of a rate of the CPR chest compressions. In addition, the temporal peak detection algorithm detects and counts CPR chest compression artifacts due to CPR chest compressions by picking up artifactual peaks caused by the CPR chest compressions in the at least one of (i) the stream of raw transthoracic impedance data and (ii) the stream of common-mode current data. Furthermore, an approximate depth of CPR chest compressions can be reflected by a magnitude of the artifactual peaks in the at least one of (i) the stream of raw transthoracic impedance data and (ii) the stream of common-mode current data. Moreover, the approximate depth of CPR chest compressions can be determined by setting adaptive thresholds. Still further, the frequency analysis algorithm applies a Fourier transform on the at least one of (i) the stream of raw transthoracic impedance data and (ii) the stream of common-mode current data and searches for an existence of a fundamental frequency corresponding to the rate of CPR chest compressions in the frequency domain.

In another embodiment, the AED device further comprises a storage device and a data output port. The storage device is configured to store one or more of (i) the at least one stream of detected compression event candidates and (ii) the at least one stream of detected compression event candidates, devoid of the identified false positive compression events. The data output port is operable to transmit the stored one or more of (i) the at least one stream of detected compression event candidates and (ii) the at least one stream of detected compression event candidates, devoid of the identified false positive compression events to an external computer for post-event analysis of the stored one or more of (i) the at least one stream of detected compression event candidates and (ii) the at least one stream of detected compression event candidates, devoid of the identified false positive compression events.

In a still further embodiment, the output device is further configured to output at least one of an aural and a visual output using the indication or the optimized stream in a subsequent period of CPR chest compressions. The output device is also configured to issue, via the at least one of the aural and the visual output, at least one of a CPR and AED device guidance instruction in response to the indication.

In accordance with another embodiment, a method for detecting at least one of a status and a quality of cardiopulmonary resuscitation chest compressions with an automated external defibrillator device from signals obtained from a pair of AED electrodes, comprises the steps of: obtaining, via a front end circuit and a pair of AED electrodes (i.e., in response to being coupled to an emergency care patient's chest), at least one of (i) a stream of raw transthoracic impedance data and (ii) a stream of common-mode current data; processing, via an analysis circuit, the at least one of (i) the stream of raw transthoracic impedance data and (ii) the stream of common-mode current data for correlated CPR chest compression artifacts through first and second processing algorithms, wherein the first processing algorithm comprises a temporal peak detection algorithm to obtain at least one stream of detected compression event candidates and wherein the second processing algorithm comprises a frequency analysis algorithm to identify false positive compression events within the at least one stream of detected compression event candidates; removing, via the analysis circuit, the identified false positive compression events from the at least one stream of detected compression event candidates; and outputting, via a user output device, an indication of at least one of a status and a quality of CPR chest compressions determined in response to the at least one stream of detected compression event candidates, devoid of the identified false positive compression events.

In another embodiment, the method includes wherein an indication of the status includes an indication that CPR chest compressions are being performed, and wherein an indication of a quality of CPR chest compressions includes an indication of a rate of the CPR chest compressions. The method further includes wherein the temporal peak detection algorithm detects and counts CPR chest compression artifacts due to CPR chest compressions by picking up artifactual peaks caused by the CPR chest compressions in the at least one of (i) the stream of raw transthoracic impedance data and (ii) the stream of common-mode current data. The method still further includes wherein an approximate depth of CPR chest compressions is reflected by a magnitude of the artifactual peaks in the at least one of (i) the stream of raw transthoracic impedance data and (ii) the stream of common-mode current data, further wherein the approximate depth of CPR chest compressions are determined by setting adaptive thresholds.

In yet another embodiment, the method includes wherein the frequency analysis algorithm applies a Fourier transform on the at least one of (i) the stream of raw transthoracic impedance data and (ii) the stream of common-mode current data and searches for an existence of a fundamental frequency corresponding to the rate of CPR chest compressions in the frequency domain.

In another embodiment, the method includes wherein obtaining further comprises obtaining both (i) the stream of raw transthoracic impedance data and (ii) the stream of common-mode current data, wherein processing further comprises processing both (i) the stream of raw transthoracic impedance data and (ii) the stream of common-mode current data to obtain respective first and second streams of detected compression event candidates and to identify false positive compression events within the respective first and second streams of detected compression event candidates, and wherein removing further comprises removing the identified false positive compression events from respective first and second streams of detected compression event candidates. The method further comprises: comparing, via the analysis circuit, the first stream of detected compression event candidates, devoid of the respective identified false positive compression events, against the second stream of detected compression event candidates, devoid of the respective identified false positive compression events, to identify an optimized stream of detected compression event candidates between the first and second streams. In addition, the outputting further comprises outputting the indication determined in response to the optimized stream of detected compression event candidates, devoid of false positive compression events. The step of comparing to identify an optimized stream of detected compression event candidates between the first and second streams comprises (i) applying a criterion to the first and second streams and (ii) selecting one of the first and second streams based upon the applied criterion to identify the optimized stream.

According to yet another embodiment, the method further comprises: determining, via an analysis circuit configured to implement an electrocardiogram (ECG) shock analysis, a shockable ECG event in the presence of CPR-related signal artifacts; and dynamically adjusting, via the ECG shock analysis circuit, a shock decision parameter or threshold criterion in response to one or more of (i) the at least one stream of detected compression event candidates, devoid of the identified false positive compression events, and (ii) the indication of the at least one of a status and a quality of CPR chest compressions.

In a still further embodiment, the method comprises storing, via a storage device, one or more of (i) the at least one stream of detected compression event candidates and (ii) the at least one stream of detected compression event candidates, devoid of the identified false positive compression events; and analyzing, via an external analyzing computer for post-event analysis, the stored one or more of (i) the at least one stream of detected compression event candidates and (ii) the at least one stream of detected compression event candidates, devoid of the identified false positive compression events.

In yet another embodiment, the outputting further comprises outputting at least one of an aural and a visual output of the indication on the AED device. In addition, the method further includes issuing, via the at least one of the aural and the visual output, at least one of a CPR and AED device guidance instruction in response to the indication.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

Figure 3:
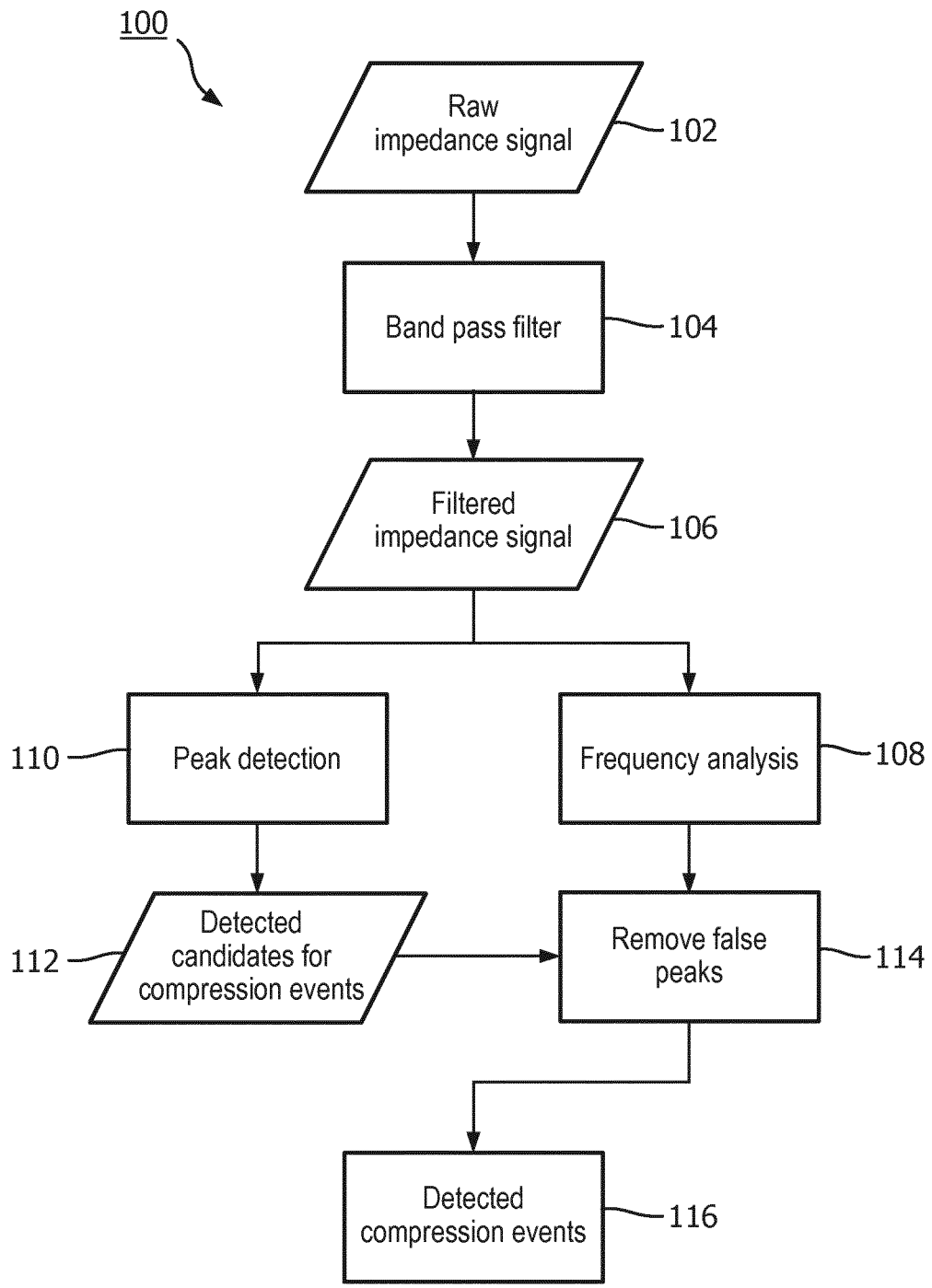
Figure 4:
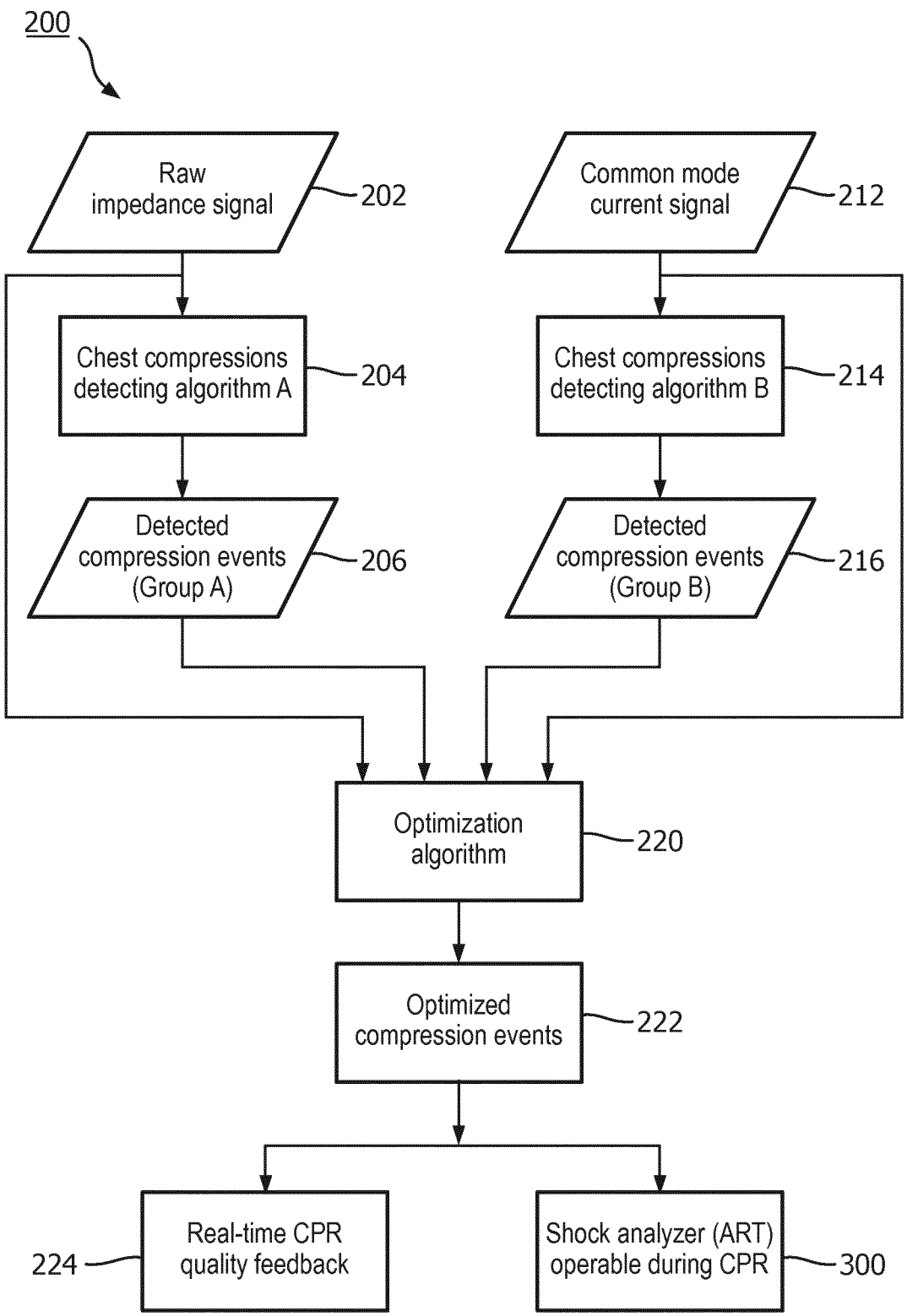

FIG. 3 is a flow diagram view of a method, which may be used with either impedance channel information and/or common-mode current channel information, for detecting at least one of a status and a quality of cardiopulmonary resuscitation chest compressions, according to one embodiment of the present disclosure; and FIG. 4 is a flow diagram view of a method, which uses both impedance channel information and common-mode current channel information, for detecting at least one of a status and a quality of CPR chest compressions, according to one embodiment of the present disclosure, and further directed to a post-rescue analysis program, such as the Event Review Pro™ software application product manufactured by Koninklijke Philips, N.V. of Andover, Mass.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to one objective, a method has been developed to detect the status/quality of chest compressions during cardiopulmonary resuscitation (CPR), by analyzing the existing measurements in AED devices without using an integrated or standalone CPR feedback device. This method can be incorporated into the lower-end AED devices which don't have a compression meter (i.e., a CPR meter), so that the responder or user can still get valuable feedback about the quality of CPR being administered, similar to what he/she could get from an integrated or standalone CPR feedback device. The method according to the embodiments of the present disclosure may also be used on higher-end devices on which the optional CPR feedback device has not been installed. The method according to the embodiments of the present disclosure provides an approach that analyzes the thoracic impedance and/or common-mode current, which can be measured with standard AED pad electrodes.

As discussed herein, when CPR chest compression is performed, highly correlated artifacts exist in the impedance and common-mode current measurements. Those artifacts reflect 1) if compression is being performed; 2) the rate of compression; and 3) the depth of compression. As the first step, detecting the existence of compression can a) remind the responder to start CPR as soon as possible if the compression is detected as "OFF"; and b) allow the system (i.e., the AED device) to choose an appropriate tuning of the diagnostic algorithm according to the status of CPR (i.e., a status of CPR determined in response to the correlated artifacts determined to exist in the impedance and common-mode current measurements during a given resuscitation and corresponding compression) to make the best shock decisions. The detection of the compression's quality, by determining its rate and/or depth, can support real-time feedback to guide the provider, as well as provide a retrospective quality review for further training.

As will be discussed herein, the detection of compressions can be performed by detecting the existence of a fundamental frequency corresponding to the rate of compression. A Fourier Transform may be applied on impedance/common-mode current signals and then the fundamental frequency can be searched in the frequency domain. Alternatively, the artifacts due to compression can be detected and counted by picking up the artifactual peaks caused by chest compression in impedance and/or common-mode current recordings (i.e., recorded signals). The depth of compression can be reflected by the magnitude of the artifactual peaks in impedance and common-mode current recordings (i.e., recorded signals). Adaptive thresholds would be set to determine the approximate depth of compression. In addition, thoracic impedance can be measured by AED devices, and common-mode current is possible to measure using standard AED pads.

Due to the varieties of the patients' position, size, the environment, the location of the shock pads, the site for performing compression, etc., sometimes the impedance can better reflect the artifacts caused by compression than the common-mode current, sometimes the opposite. The advantage of utilizing both measurements will result in better detection of compression than using only one measurement. In order to use both measurements, the following strategies may by applied: 1) to analyze the two measurements separately, and draw final conclusions based on results from both channels; 2) to periodically check the quality of signals in two channels, and analyze the channel which has better quality; 3) to apply numerical methods to combine the two channels, and then analyze the combined signal.

In the following discussion with reference to FIGS. 1 and 2, the embodiments of the present disclosure will be discussed in the context of an actual use case involving a sudden cardiac arrest (SCA) situation. However, the embodiments of the present disclosure can also be applied to other types of situations, for example, a training situation.

Figure 1:
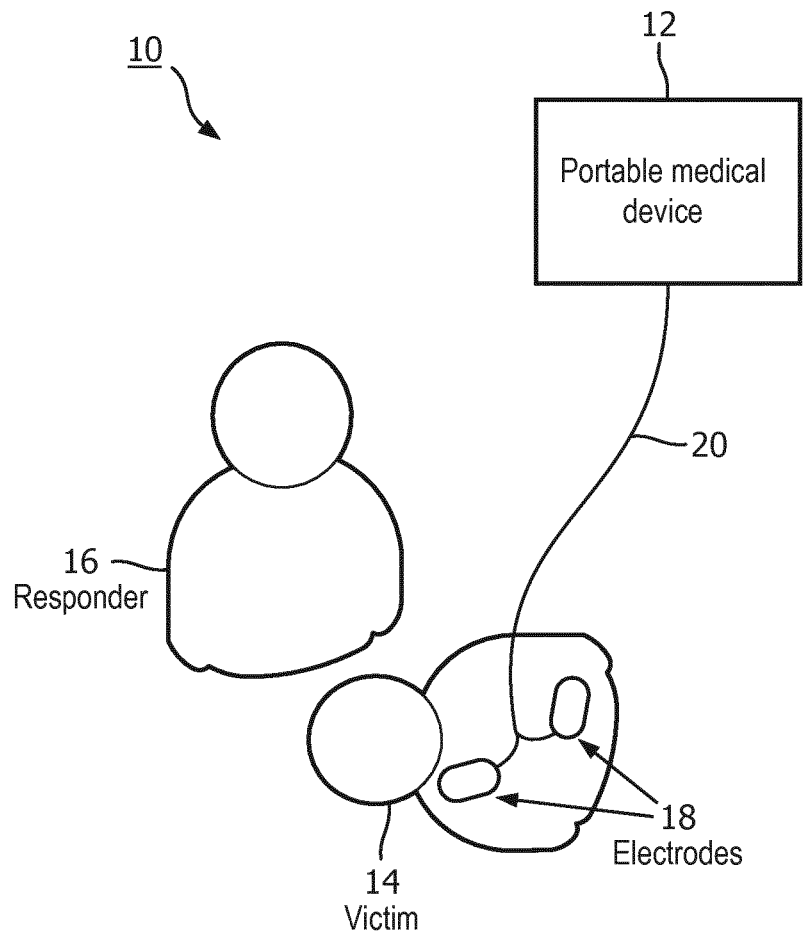
FIG. 1 is an illustrative view showing a portable medical device having a feature for detecting at least one of a status and a quality of cardiopulmonary resuscitation chest compressions according to an embodiment of the present disclosure, the figure further illustrating a victim and a responder.

Turning now to FIG. 1, there is shown an illustrative view 10 showing a portable medical device 12 having a feature for detecting at least one of a status and a quality of cardiopulmonary resuscitation chest compressions according to an embodiment of the present disclosure. The figure further illustrates a victim 14 of sudden cardiac arrest and a responder 16 (e.g., a person using the device 12 and/or administering CPR). In this embodiment, the portable medical device 12 comprises an automated external defibrillator device equipped with a pair of AED electrodes 18 coupled to the portable medical device 12 via power/signal lines or patient leads 20. In addition, the pair of AED electrodes 18 is shown as being applied to the victim's chest, in preparation for administration of an electrocardiogram (ECG) shock, further in response to a detection of an ECG shockable event.

Figure 2:
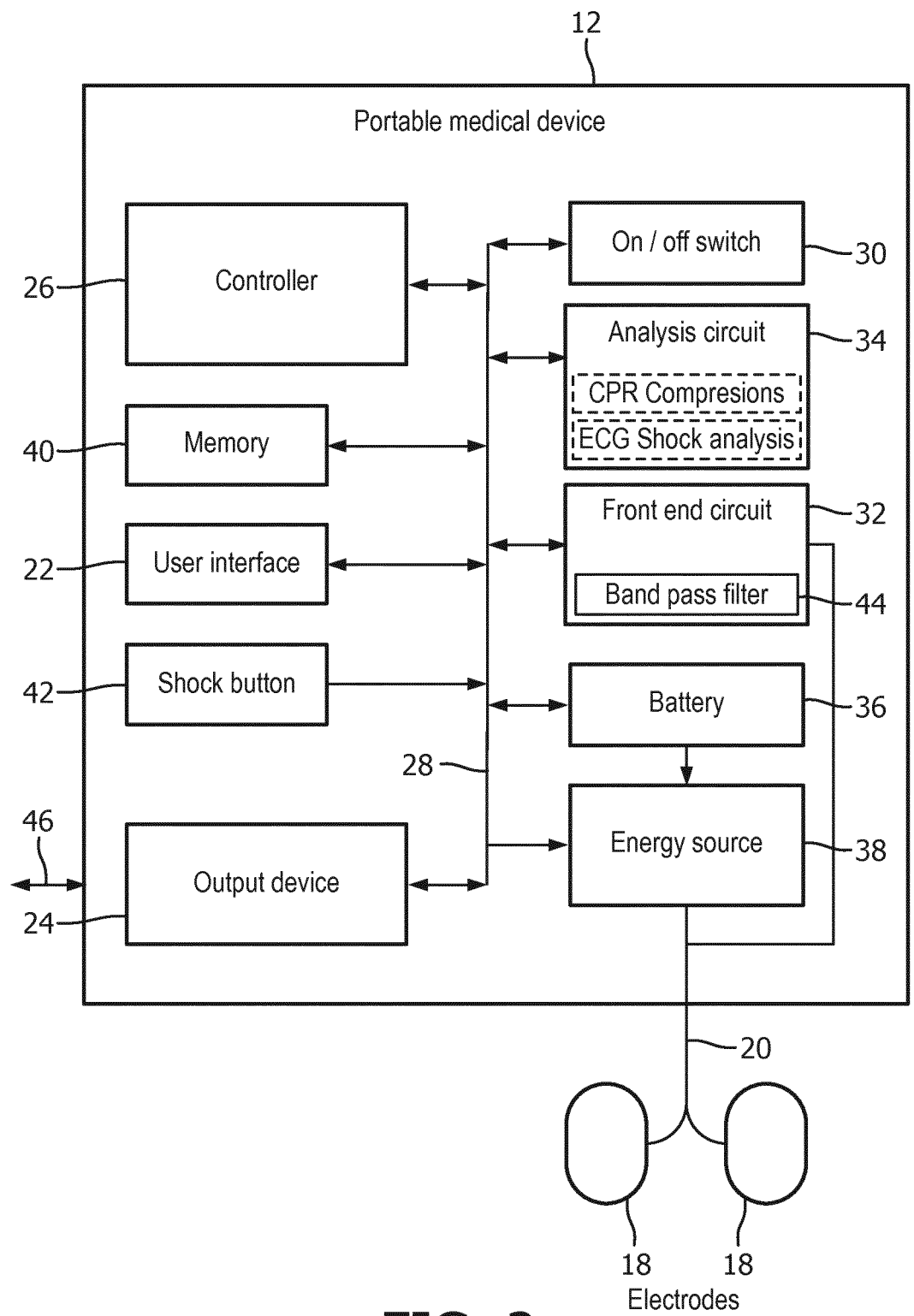
FIG. 2 is a block diagram view of the portable medical device having a feature for detecting at least one of a status and a quality of CPR chest compressions in further detail, according to an embodiment of the present disclosure.

Turning now to FIG. 2, there is shown a block diagram view of the portable medical device 12 having a feature for detecting at least one of a status and a quality of cardiopulmonary resuscitation chest compressions in further detail, according to an embodiment of the present disclosure. In one embodiment, the portable medical device 12 comprises an AED device that includes at least a user interface 22, an output device 24, and a controller 26. The user interface 22 is configured for at least initiating the method according to one or more of the various embodiments discussed herein, and comprises any suitable user interface operatively coupled to at least the controller 26, via signal lines 28, for use in connection with and/or during an emergency situation, as discussed further herein. For example, user interface 22 can comprise a graphical user interface operatively coupled to at least the controller 26, via signal lines 28, for use in connection with a given portable medical device implementation and/or application, e.g., during an emergency, as discussed further herein. In addition, user interface 22 may also comprise at least one selected from the group consisting of an input/output device, a tactile output device, a touch screen, an optical display, a microphone, a keypad, a keyboard, a pointing device, an image capture device, a video camera, an audio output device, and any combination thereof, determined as appropriate according to the requirements of a given portable medical device implementation and/or application.

As will be understood from the disclosure herein, the output device 24 is configured to output an indication of at least one of a status and a quality of cardiopulmonary resuscitation chest compressions determined in response to the at least one stream of detected compression event candidates, devoid of identified false positive compression events. In one embodiment, the output device 24 comprises any suitable output device operatively coupled to at least the controller 26, via signal lines 28, for use in connection with and/or during an emergency and/or other situation, as discussed further herein. For example, output device 24 can comprise at least one selected from the group consisting of an audio and/or video output device, a tactile output device, an optical device panel and/or display, and any combination thereof, determined as appropriate according to the requirements of a given portable medical device implementation and/or application.

As noted above, the controller 26 operatively couples to the user interface 22 and the output device 24 via suitable signal lines, indicated via reference numeral 28. In one embodiment, controller 26 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given portable medical device implementation and/or application. Controller 26 can further comprise one or more of the various modules as discussed herein. Additional details regarding the controller 26 will be provided herein below with reference to the Figures.

With reference still to FIG. 2, the portable medical apparatus 12 can further comprise one or more of an ON/OFF switch 30, a front end circuit module 32, an analysis circuit module 34, a battery 36, an energy source 38, memory 40, and shock button 42 (e.g., for activating the administration of a shock via AED pad electrodes). Each of the one or more of the ON/OFF switch 30, front end circuit module 32, analysis circuit module 34, battery 36, energy source 38, memory 40, and shock button 42 is operatively coupled to at least the controller 26, e.g., via signal lines 28. The ON/OFF switch 30 comprises any suitable switch for powering the portable medical apparatus 12 between ON and OFF.

The front end circuit module 32 comprises any suitable integrated circuit, discrete analog or digital circuit components, hardware, software, firmware, or any combination thereof, for performing various functions as discussed herein, further according to the requirements of a given portable medical device implementation and/or application. In one embodiment, the front end circuit module 32 is configured to obtain, via a pair of AED electrodes coupled to an emergency care patient's chest, at least one of (i) a stream of raw transthoracic impedance data and (ii) a stream of common-mode current data, as discussed herein. For example, the front end circuit module 32 can be implemented as a computer program module. It is understood that the described modules may be computer program modules which are rendered in a non-transitory computer-readable medium. In one embodiment, front end circuit module 32 also comprises a band pass filter 44, as will be discussed further herein.

The analysis circuit module 34 comprises any suitable integrated circuit, discrete analog or digital circuit components, hardware, software, firmware, or any combination thereof, for performing various functions as discussed herein, further according to the requirements of a given portable medical device implementation and/or application. In one embodiment, the analysis circuit module 34 is configured to (a) process the at least one of (i) the stream of raw transthoracic impedance data and (ii) the stream of common-mode current data for correlated CPR chest compression artifacts through first and second processing algorithms, wherein the first processing algorithm comprises a temporal peak detection algorithm to obtain at least one stream of detected compression event candidates and wherein the second processing algorithm comprises a frequency analysis algorithm to identify false positive compression events within the at least one stream of detected compression event candidates, and (b) remove the identified false positive compression events from the at least one stream of detected compression event candidates, as discussed herein. In another embodiment, the analysis circuit module 34 is also configured to implement an algorithm that analyzes an ECG for a shockable condition while CPR chest compressions are ongoing, as discussed herein. Furthermore, the analysis circuit module 34 can be implemented as a computer program module. It is understood that the described modules may be computer program modules which are rendered in a non-transitory computer-readable medium.

In one embodiment, battery 36 can comprise any suitable power source or power supply for a given portable medical device implementation and/or application. In addition, energy source 38 can comprise any suitable power source or power supply for a given portable medical device implementation and/or application. For example, for a portable medical device comprising an AED device, the energy source 38 can comprise high voltage capacitor suitable for storing energy effective in defibrillating shocks, where the capacitor is charged by battery 36 through a charging circuit (not shown). Furthermore, memory 40 can comprise any suitable memory and/or storage device, operatively coupled to at least the controller 26, for at least storing information thereto, and further for at least subsequently retrieving the information there from.

The portable medical apparatus 12 can further comprise a pair of AED pad electrodes 18 operatively coupled to energy source 38, for administration of an electrical shock during use of the portable medical device 12 as an AED device. The pair of AED pad electrodes 18 is also operatively coupled to the front end circuit module 32, via patient leads 20, as discussed further herein.

Referring still to FIG. 2, portable medical device 12 further comprises a data output port 46. The data output port 46 is operable to transmit a stored one or more of (i) the at least one stream of detected compression event candidates and (ii) the at least one stream of detected compression event candidates, devoid of the identified false positive compression events to an external computer (not shown) for post-event analysis, as discussed further herein.

The embodiments of the present disclosure recognize that when CPR is performed, highly correlated artifacts exist in the transthoracic impedance and common-mode current measurements obtained with the use of the AED device's chest electrodes. Those artifacts reflect i) if CPR compressions are being performed, and; ii) the rates (and/or depths) of those CPR compressions. Properly detected and analyzed, these parameters (or artifacts in the transthoracic impedance and common-mode current) can be used to indicate a measure of CPR quality. In addition, a provision for determining a compressions hands-on time and compression rate can support real-time feedback to guide an urgent care provider or responder administering CPR. Furthermore, the compressions hands-on time and compression rate may be retained in computer memory for subsequent use, such as, in a post-event analysis and/or retrospective quality review for further training. The method and apparatus according to the embodiments of the present disclosure also advantageously allows an AED device and/or system to select an appropriate tuning of the device and/or a system diagnostic algorithm according to the status of CPR chest compressions being administered in order to render the best ECG shock decisions.

In one embodiment, the artifacts due to CPR chest compressions can be detected and counted by picking up the artifactual peaks caused by chest compressions in one or more of the transthoracic impedance and/or common-mode current measurement signals and/or recordings. Alternatively, the CPR chest compressions (or artifacts due to CPR compressions) can also be detected by determining the existence of a fundamental frequency in the measurement signals, the fundamental frequency corresponding to the rate of compression in the frequency domain. A Fourier Transform may be applied to the impedance/common-mode current signals, from which the fundamental frequency can be searched in the frequency domain.

In operation, the CPR chest compressions are first detected in the temporal domain by using a peak detection algorithm. Then, a frequency analysis is performed to search for the fundamental frequency. If the fundamental frequency cannot be determined in a certain predetermined interval, then the corresponding compression peaks within the predetermined interval detected previously (i.e., as determined via the peak detection algorithm) are considered to be false positives and thereafter removed from further consideration. On the other hand, if the fundamental frequency can be determined in the certain pre-determined interval, then the corresponding compression peaks within the predetermined interval are considered optimized compression peaks. Accordingly, the optimized compression peaks which remain are used to calculate the compression rates and on/off intervals of CPR chest compressions.

Turning now to FIG. 3, there is shown a flow diagram view of a method 100, which may be used with either impedance channel information and/or common-mode current channel information, for detecting at least one of a status and a quality of cardiopulmonary resuscitation chest compressions, according to one embodiment of the present disclosure. In particular, the process flow diagram of FIG. 3 illustrates one embodiment of a method for detecting "true" CPR chest compressions, each compression being deemed an "event". The FIG. 3 process uses an input of a raw impedance signal at input step 102 that is obtained via the AED front end signal processing circuit 32 from two or more electrodes 18 that are placed upon the patient's torso. The raw impedance signal may optionally be filtered at filtering step 104 with a band pass filter 44 or via other suitable known signal filter methods.

The resulting filtered impedance signal at step 106 is then analyzed in two different ways. Firstly, a temporal based algorithm is applied at peak detection step 110 to determine candidates from the impedance signal stream that may pertain to a CPR-related compression artifact. The candidates are then provided to a detected candidates step 112.

Secondly, a frequency based analysis method is applied to the impedance signal stream at step 108 to determine artifact events that are likely to be false positives. As the candidates from step 112 are fed into a screening step 114, the output from step 108 causes the candidates that are likely to be false positives to be removed from the stream. The final stream of detected compression events is then output at output step 116.

While the process of FIG. 3 has been discussed with respect to using the transthoracic impedance signal, the process may also be similarly used with an input of the common-mode current signal that is captured by the AED electrodes 18 and the AED front end signal processing circuit 32. As used herein, common-mode current refers to a current that flows equally in both patient leads 20 in a circuit that includes capacitive coupling between the patient and the AED device through earth ground. Changes in the static electrical field around the patient produce this current, and are related to the motion associated with CPR chest compressions. In addition, the resulting output at step 116 is of detected compression events with removed false peaks. The two data sets of compression events, i.e., from transthoracic impedance and common-mode current, are then stored in computer memory in a time-correlated fashion.

With reference now to FIG. 4, there is shown a flow diagram view of a method 200, which uses both impedance channel information and common-mode current channel information, for detecting at least one of a status and a quality of CPR chest compressions, according to one embodiment of the present disclosure, and further directed to a post-rescue analysis program, such as the Event Review Pro™ software application product manufactured by Koninklijke Philips, N.V. of Andover, Mass. In particular, FIG. 4 illustrates a flow diagram of the inventive method which further uses the two data sets of detected CPR compression events to provide an output that is useful to the user or urgent care provider, or useful to an administrator performing post-event analysis, or useful to a shock analysis algorithm (e.g., ART) that is operating during the CPR chest compressions interval. Steps 202, 204, and 206 pertain to the FIG. 3 process steps 102 through 116 as applied to the transthoracic impedance signal, discussed herein above. Steps 212, 214 and 216 pertain to the FIG. 3 process steps 102 through 116 as applied to the simultaneously obtained common-mode current signal, similarly as discussed herein above.

The two data sets of detected CPR chest compression events are compared at optimization step 220. The quality of the impedance recording and the common-mode current recording can be evaluated by checking (i.e., evaluating) the amplitude, stability, etc., of the respective recordings. In one embodiment, three quality levels can be defined: "good", "fair" and "bad". If the quality level of the impedance signal is better than the quality level of the common-mode current signal or their quality levels are the same, then the detected CPR chest compression events in the impedance signal are preferably used as the most reliable set (or optimized set of CPR chest compression events). On the other hand, if the quality level of the impedance signal is lower than that of the common-mode current signal, then the detected compression events in the common-mode current signal are used as the most reliable set (or optimized set of compression events). In most cases, it is expected that the impedance signal stream of compression events will be determined at step 220 to be the most reliable set. In some cases, however, the common-mode current signal stream of compression events will be determined at step 220 to be the most reliable set.

In other words, the signal analysis circuitry (i.e., analysis circuit or module 34) is configured to select the set of CPR chest compression events detected in the impedance signal in response to the impedance signal stream being determined as the most reliable data set (or optimized set). In addition, the signal analysis circuitry (i.e., analysis circuit or module 34) is further configured to select the set of CPR chest compression events detected in the common-mode current signal in response to the common-mode current signal stream being determined as the most reliable data set (or optimized set). The most reliable set of the two data sets is then selected at step 220 and provided to the output step 222 for further use. For example, the data set or mode showing the most reliable CPR chest compressions set may be used in subsequent periods of CPR chest compressions, i.e. after a "hands-off" ECG analysis and/or a defibrillation shock.

In another embodiment, the common-mode current signal from step 212 may be used directly at comparing/optimization step 220 as described above and without first filtering and processing the signal. Similarly, the raw transthoracic impedance signal from step 202 may be used directly at comparing/optimization step 220 as described above and without first filtering and processing the signal.

Exemplary uses with respect to the most reliable data set are for post-event CPR analysis, including post-event CPR analysis with a software based analysis program such as the Event Review Pro™ software previously described. Another exemplary use with respect to the most reliable data set is for providing real-time feedback (step 224) as to (i) presence and (ii) rate of CPR compressions being provided. In this later case, aural and visual feedback may be provided, via an output device 24, to the AED user or urgent care provider 16 to guide the user to a more optimal CPR chest compression performance, or to assure the AED user that the ongoing CPR compressions are adequate. The aural and visual feedback may be provided via a user output, e.g., on an AED display, by flashing light, by beeper, or by aural instructions via a speaker. Some exemplary CPR feedback instructions can include one or more of i) aural instructions such as "compress more quickly," "compress more slowly," "press hard and fast," ii) visual feedback such as a marker in a linear scale indicating compression rate above, within, or below the preferred rate, and iii) any combinations thereof.

According to further embodiments, the inventive methods of the present disclosure may be incorporated into an AED, and in particular to an AED which uses an algorithm that analyzes an ECG for a shockable condition while CPR chest compressions are ongoing. Thus, another exemplary use with respect to the most reliable or optimized data set may be to provide an input at analysis algorithm input step 300 to an ECG shock analyzer of analysis circuit 34. The ECG shock analyzer of analysis circuit 34 may use the input of compression events (i.e., the most reliable or optimized data set) to dynamically adjust its shock decision threshold criteria in cases of CPR rates which are outside of protocol standards, e.g. rates significantly lower than 100/minute or significantly higher than 120/minute, or perhaps in cases where CPR is not being provided when it should be, or perhaps in cases where CPR is being provided when it should not be. The input of the optimized data set of compression events thus enables a more accurate determination of a "shock advised" condition in the AED, with fewer false positive determinations. Accordingly, higher false positive rates, as discussed above in the previously presented example, with respect to the condition of abnormally high CPR chest compression rates is thus advantageously avoided.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure may also be applicable for use in monitor/defibrillators. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An automated external defibrillator (AED) device having a feature for detecting at least one of a status and a quality of cardiopulmonary resuscitation (CPR) chest compressions, characterized in that the AED device comprises:
   a front end circuit configured to obtain, via a pair of AED electrodes, at least one of (i) a stream of raw transthoracic impedance data and (ii) a stream of common-mode current data,
   an analysis circuit configured to
      (a) process at least one of (i) the stream of raw transthoracic impedance data and (ii) the stream of common-mode current data, for correlated CPR chest compression artifacts through first and second processing algorithms, wherein the first processing algorithm comprises a temporal peak detection algorithm to obtain at least one stream of detected compression event candidates and wherein the second processing algorithm comprises a frequency analysis algorithm to identify false positive compression events within the at least one stream of detected compression event candidates, and
      (b) remove the identified false positive compression events from the at least one stream of detected compression event candidates to generate at least one stream of detected compression events that is devoid of the identified false positive compression events;
   determining at least one of a status and a quality of CPR chest compressions for the at least one stream of detected compression events that is devoid of the identified false positive compression events; and an output device configured to output an indication of at least one of the status and a quality of CPR chest compressions.

2. The device of claim 1, wherein the temporal peak detection algorithm detects and counts CPR chest compression artifacts due to CPR chest compressions by picking up artifactual peaks caused by the CPR chest compressions in the at least one of (i) the stream of raw transthoracic impedance data and (ii) the stream of common-mode current data, further wherein an approximate depth of CPR chest compressions is reflected by a magnitude of the artifactual peaks in the at least one of (i) the stream of raw transthoracic impedance data and (ii) the stream of common-mode current data, further wherein the approximate depth of CPR chest compressions is determined by setting adaptive thresholds, and wherein the frequency analysis algorithm applies a Fourier transform on the at least one of (i) the stream of raw transthoracic impedance data and (ii) the stream of common-mode current data, and searches for an existence of a fundamental frequency corresponding to a rate of CPR chest compressions within the frequency domain.

3. The device of claim 1, further comprising:
a storage device configured to store one or more of (i) each respective stream of detected compression event candidates and (ii) each respective stream of detected compression event candidates, devoid of the identified false positive compression events; and
a data output port operable to transmit the stored one or more of (i) each respective stream of detected compression event candidates and (ii) each respective stream of detected compression event candidates, devoid of the identified false positive compression events to an external computer for post-event analysis of the stored one or more of (i) each respective stream of detected compression event candidates and (ii) each respective stream of detected compression event candidates, devoid of the identified false positive compression events.

4. The device of claim 1, wherein the output device is further configured to output at least one of an aural and a visual output to issue at least one of a CPR and AED device guidance instruction in response to the indication.

5. An automated external defibrillator (AED) device having a feature for detecting at least one of a status and a quality of cardiopulmonary resuscitation (CPR) chest compressions, characterized in that the AED device comprises:
a front end circuit configured to obtain, via a pair of AED electrodes, (i) a stream of raw transthoracic impedance data and (ii) a stream of common-mode current data,
an analysis circuit configured to
(a) process both (i) the stream of raw transthoracic impedance data and (ii) the stream of common-mode current data to obtain respective first and second streams of detected compression event candidates and to identify false positive compression events within the respective first and second streams of detected compression event candidates, and
(b) remove the identified false positive compression events from respective first and second streams of detected compression event candidates, and
(c) compare the first stream of detected compression event candidates, devoid of the respective identified false positive compression events, against the second stream of detected compression event candidates, devoid of the respective identified false positive compression events, to identify an optimized stream of detected compression event candidates between the first and second streams;
determining at least one of a status and a quality of CPR chest compressions for the optimized stream of detected compression events; and
an output device configured to output the indication of at least one of a status and a quality of CPR chest compressions determined in response to the optimized stream of detected compression event candidates, devoid of the identified false positive compression events.

6. The device of claim 5, wherein the analysis circuit identifies the optimized stream of detected compression event candidates between the first and second streams by (i) applying a criterion to the first and second streams and (ii) selecting one of the first and second streams based upon the applied criterion to identify the optimized stream.

7. The device of claim 6, wherein the criterion comprises a determined autocorrelation strength similar to a predicted CPR rate period.

8. The device of claim 6, wherein the analysis circuit further comprises an electrocardiogram (ECG) shock analysis circuit configured to (i) determine a shockable ECG event in response to an ECG signal obtained via the pair of AED electrodes in the presence of CPR-related signal artifacts and (ii) dynamically adjust a shock decision parameter in response to one or more of (a) the optimized stream of detected compression event candidates, devoid of the identified false positive compression events, and (b) the indication of the at least one of a status and a quality of CPR chest compressions.

9. The device of claim 6, wherein the optimized stream of detected compression event candidates is indicative of a CPR chest compression rate that is outside of a CPR protocol standard rate.

10. The device of claim 6, wherein the indication of the status includes an indication that CPR chest compressions are being performed, and wherein the indication of the quality of CPR chest compressions includes an indication of a rate of the CPR chest compressions.

* * * * *